United States Patent
Kramer et al.

(10) Patent No.: US 9,353,143 B1
(45) Date of Patent: *May 31, 2016

(54) ECDYSTERONE COMPOUNDS

(71) Applicant: ThermoLife International, LLC, Phoenix, AZ (US)

(72) Inventors: Ronald Kramer, Phoenix, AZ (US); Alexander Nikolaidis, New Kallikratia (GR)

(73) Assignee: ThermoLife International, LLC

( * ) Notice: Subject to any disclaimer, the term of this patent is extended or adjusted under 35 U.S.C. 154(b) by 0 days.

This patent is subject to a terminal disclaimer.

(21) Appl. No.: 13/731,549

(22) Filed: Dec. 31, 2012

Related U.S. Application Data

(63) Continuation of application No. 12/509,878, filed on Jul. 27, 2009, now Pat. No. 8,343,946.

(51) Int. Cl.
| | |
|---|---|
| *A61K 31/56* | (2006.01) |
| *C07J 9/00* | (2006.01) |
| *C07C 53/124* | (2006.01) |
| *C07C 53/126* | (2006.01) |

(52) U.S. Cl.
CPC ............... *C07J 9/00* (2013.01); *C07C 53/124* (2013.01); *C07C 53/126* (2013.01)

(58) Field of Classification Search
USPC ........................................................ 514/171
See application file for complete search history.

(56) References Cited

PUBLICATIONS

Meraz (Ecdysterone works by increasing nitrogen retention and increasing protein synthesis (that is why you should increase yourdaily intake of protein while using this product, Mar. 7, 2002, p. 1.*

Bruno (20-Hydroxyecdysone: The Pro-Anabolic, Plant Steriod, Huntington College of Health Sciences, 2001, pp. 1-3).*
Miescher (The activation of the Male Sex Hormones, 1936, pp. 1977-1990).*
"Plant Based Anabolics" http://www.mindandmuscle.net/articles/plan-anabolics/ Jun. 13, 2009.
"1-TU" http://www.nicemuscle.com1-tu-80551.htm/.
"1-TU" http://www.netrition.com/nutrex_1tu_page.html.
Stoppani (Best Supps for Mass, 2008, the Altoona Area's Best Source for Supplements, pp. 1-2, www.redlinenutrition.net/Mass-Building-Supplements.php, obtained Nov. 17, 2010).
Deca Durabolin (www.steriodsrx.com/articles/decs_durabolin.cfm, copyright 2008, obtained Nov. 17, 2010).
Roberts (Anabolic Steriod Esters, 1999, pp. 1-5, www.mesomorphosiscom/articles/pharmacology/anabolic-steriod-ster.htm, obtained Nov. 17, 2010).
V.N. Syrov et al., Study of The Structure—Anabolic Activity Relationship for Phtyoecdysteroids Extracted From Some Plants of Central Asia, Pharmaceutical Chemistry Journal, vol. 35, No. 12, 2001.
Maria Bathori et al., Phytoecdysteroids—From Isolation to Their Effects on Humans, Current Medicinal Chemistry, 2005, 12, 153-172.

\* cited by examiner

*Primary Examiner* — Kathrien Cruz

(74) *Attorney, Agent, or Firm* — Booth Udall Fuller, PLC

(57) ABSTRACT

An ecdysterone compound is described. An ecdysterone compound may include ecdysterone and decanoic acid. An ecdysterone compound may further include ecdysterone and isobutyric acid. An ecdysterone compound may comprise a physiologically active salt or ester of ecdysterone. An ecdysterone compound may further comprise a physiologically active salt or ester of decanoic acid. Alternatively, an ecdysterone compound may include a physiologically active salt or ester of isobutyric acid.

10 Claims, No Drawings

ECDYSTERONE COMPOUNDS

CROSS REFERENCE TO RELATED APPLICATIONS

This application is a continuation application of the earlier U.S. Utility Patent Application to Ronald Kramer, et. al. entitled "Ecdysterone Compounds," application Ser. No. 12/509,878, filed Jul. 27, 2009, now pending, the disclosure of which is hereby incorporated entirely herein by reference.

BACKGROUND

1. Technical Field

Aspects of this document relate generally to Ecdysterone Compounds.

2. Background

Ecdysteroids are a group of 2,3,14-trihydroxy-Δ-7-6-ketosteroids. There has been extensive research on the effects of oral ecdysterone supplementation on humans. The documented effects of ecdysteroids and ecdysteroid compositions are wide-ranging.

SUMMARY

In one aspect, an ecdysterone compound comprises ecdysterone and decanoic acid.

Implementations may comprise one or more of the following. The ecdysterone may comprise a physiologically active salt of ecdysterone. The ecdysterone may comprise a physiologically active ester of ecdysterone. The decanoic acid may comprise a physiologically active salt of decanoic acid. The decanoic acid may comprise a physiologically active ester of decanoic acid.

In another aspect, an ecdysterone compound comprises ecdysterone and isobutyric acid.

Implementations may comprise one or more of the following. The ecdysterone may comprise a physiologically active salt of ecdysterone. The ecdysterone may comprise a physiologically active ester of ecdysterone. The isobutyric acid may comprise a physiologically active salt of isobutyric acid. The isobutyric acid may comprise a physiologically active ester of isobutyric acid.

In another aspect, a method for increasing in a human or animal one of: bioavailability of ecdysterone; half-life of ecdysterone; and distribution to skeletal muscle tissue of ecdysterone, the method comprises administering a pharmaceutically effective amount of an ecdysterone compound to the human or animal.

Implementations may comprise one or more of the following. Administering a pharmaceutically effective amount of an ecdysterone compound to the human or animal may comprise administering ecdysterone decanoate in a range from about to about 0.1 milligram per kilogram of body weight to about 1.0 milligram per kilogram of body weight. Administering a pharmaceutically effective amount of an ecdysterone compound to the human or animal may comprise administering ecdysterone decanoate in a range from about to about 1.0 milligram per kilogram of body weight to about 10.0 milligrams per kilogram of body weight. Administering a pharmaceutically effective amount of an ecdysterone compound to the human or animal may comprise an intravenous or intramuscular injection. Administering a pharmaceutically effective amount of an ecdysterone compound to the human or animal may comprise oral administration. Administering a pharmaceutically effective amount of an ecdysterone compound to the human or animal may comprise administering ecdysterone isobutyrate in a range from about to about 0.1 milligram per kilogram of body weight to about 1.0 milligram per kilogram of body weight. Administering a pharmaceutically effective amount of an ecdysterone compound to the human or animal may comprise administering ecdysterone isobutyrate in a range from about to about 1.0 milligram per kilogram of body weight to about 10.0 milligrams per kilogram of body weight. Administering a pharmaceutically effective amount of an ecdysterone compound to the human or animal may comprise an intravenous or intramuscular injection. Administering a pharmaceutically effective amount of an ecdysterone compound to the human or animal may comprise oral administration. Administering a pharmaceutically effective amount of an ecdysterone compound to the human or animal may comprise administering one of ecdysterone decanoate and ecdysterone isobutyrate from about to about 0.1 milligram per kilogram of body weight to about 10.0 milligrams per kilogram of body weight.

The foregoing and other aspects, features, and advantages will be apparent to those artisans of ordinary skill in the art from the DESCRIPTION and DRAWINGS, and from the CLAIMS.

DESCRIPTION

Overview

As noted above, ecdysteroids are a group of 2,3,14-trihydroxy-Δ-7-6-ketosteroids. A comprehensive listing of currently-known ecdysteroids, as well as their chemical structures and sources, may be viewed at www.ecdybase.org. Ecdysterone, also variously known as 20-Hydroxyecdysone or "20E," is just one representative species of the genus of ecdysteroids. While the particular implementations that follow describe non-limiting examples involving ecdysterone (alone or in conjunction with other substances), it will be understood that the disclosures contained within this document may equally be applied to ecdysteroids other than ecdysterone, as well as their single administration forms, their physiologically active salts or esters, their combinations with their various salts, their tautomeric, polymeric and/or isomeric forms, their analog forms, their derivative forms, and/or their decarboxylation products.

Accordingly, the disclosures contained within this document may apply to ecdysteroids other than ecdysterone, such as by way of non-limiting example, the following ecdysteroids: abutasterone25-acetoxy-20-hydroxyecdysone 3-o-; beta;-d-glucopyranoside; acetylpinnasterol; achyranthesterone; ajugacetalsterone a; ajugacetalsterone b; ajugalide e; ajugasterone b; ajugasterone b; ajugasterone c; ajugasterone c 3; 22-diacetonide; ajugasterone c 22-ethylidene; acetal; ajugasterone c 22-monoacetonide; ajugasterone d; amarasterone a; amarasterone b; asteraster b; atrotosterone a; atrotosterone b; atrotosterone c; blechnoside a; blechnoside b; bombycosterol; bombycoster 3-phosphate; brahuisterone; calonysterone; calvaster a; calvaster b; canescensterone; capitasterone; carpesterol; carthamosterone; carthamosterone a; carthamosterone b; castasterone; cheilanthone a; cheilanthone b; coronatasterone; cyanosterone a; cyasterone; cyasterone 3-acetate; cyasterone 22-acetate; cyasterone 3-monoacetonide; cyathisterone; dacryhainansterone; decumbesterone a; dehydroajugalactone; dehydroajugalactone; dehydroamarasterone b; dehydrocyasterone 2-glucoside; 3-dehydroecdysone; 2-dehydro-3-epi-20-hydroxyecdysone; and/or 22-dehydro-12-hydroxycyasterone.

In addition to the foregoing, the disclosures contained within this document may apply to ecdysteroids other than ecdysterone, such as by way of non-limiting example, the following ecdysteroids: dehydro-20-hydroxyecdysone; 3-dehydro-20-hydroxyecdysone; dehydro-242-hydroxymakisterone c dehydro-12-hydroxy-29-nor-cyasterone; dehydro-12-hydroxy-29-nor-sengosterone; dehydro-12-hydroxy-sengosterone; (28)-dehydromakisterone a; 2-dehydropoststerone; 24-dehydroprecyasterone; 2-deoxycastasterone; 22-deoxy-21-dihydroxyecdysone; 22-deoxy-26-dihydroxyecdysone; 2-deoxy-26-dihydroxyecdysone; 3-deoxy-1α 20-dihydroxyecdysone; 2-deoxy-20-dihydroxyecdysone 2-deoxy-polypodine b; 2-deoxyecdysone; deoxyecdysone; deoxyecdysone; deoxyecdysone; 2-deoxyecdysone 3-acetate; 2-deoxyecdysone 22-acetate; 2-deoxyecdysone 22-adenosine-monophosphate; 2-deoxyecdysone 22-benzoate; 2-deoxyecdysone 3-4-(1-β-d-glucopyranosyl)-ferulate; 2-deoxyecdysone 22-β-d-glucoside; 25-deoxyecdysone 22-o-β-d-glucopyranoside; 2-deoxyecdysone 22-phosphate; 2-deoxyecdysone 25-rhamnoside; (5α)-2-deoxy-21-hydroxyecdysone; 2-deoxy-20-hydroxyecdysone; 22-deoxy-26-hydroxyecdysone; 14-deoxy-20-hydroxyecdysone; 2-deoxy-21-hydroxyecdysone; 2-deoxy-20-hydroxyecdysone 25-acetate; 2-deoxy-20-hydroxyecdysone 22-acetate; (5α)-2-deoxy-20-hydroxyecdysone 3-acetate; 2-deoxy-20-hydroxyecdysone 3-acetate; 2-deoxy-20-hydroxyecdysone 22-benzoate; and/or 2-deoxy-20-hydroxyecdysone 3-crotonate.

Additionally, the disclosures contained within this document may further apply to ecdysteroids other than ecdysterone, such as by way of non-limiting example, the following ecdysteroids: 2-deoxy-20-hydroxyecdysone 3-4-(1-β-d-glucopyranosyl-ferulate; 2-deoxy-20-hydroxyecdysone 22-diacetate; 2-deoxy-20-hydroxyecdysone 3-glucoside; 2-deoxy-20-hydroxyecdysone 22-monoacetonide; 2-deoxy-20-hydroxyecdysone 22-phosphate; 22-deoxy-20-hydroxyecdysone 3-phosphate; 2-deoxy-20-hydroxyecdysone-22-glucoside; 2-deoxy-20-hydroxyecdysone-3-o-benzoate; 25-deoxy-20-hydroxyecdysonoic acid; 22-deoxyinokosterone; (5α)-2-deoxyintegristerone a; 2-deoxyintegristerone a; 22-deoxyintegristerone a; (5α)-22-deoxyintegristerone a; 5-deoxykaladasterone 22-acetonide; 20-deoxymakisterone a 24-methyl-ecdysone; 1 2-deoxypolypodine b 3β-d-glucoside; deoxyviperidone 5α-ket; diauluster a; diauluster b; 22-didehydrotaxisterone; 1 25-dideoxyecdysone; 22-dideoxyecdysone; 22-dideoxy-20-hydroxyecdysone; 22-dideoxy-23-hydroxyecdysone; 22-dideoxy-20-hydroxyecdysone 3β-o-β-d-glucopyranoside; 1 22-dideoxy-20-hydroxyecdysone 3-phosphate; 1 22-dideoxy-23-hydroxyecdysone 3-phosphate; 28-diepi-cyasterone; 8-dihydroajugasterone c; dihydropoststerone; 1 dihydrorubrosterone; (5α)-dihydrorubrosterone; 29-dihydroxycapitasterone; (20r)-1α 20-dihydroxyecdysone; 9β 20-dihydroxyecdysone; 1 9α 20-dihydroxyecdysone; 1 26-dihydroxyecdysone podecdysone c; 1 26-dihydroxyecdysone 22-acetate; 1 26-dihydroxyecdysone 22-diacetate; 1 26-dihydroxyecdysone 22-diacetate; 1 26-dihydroxyecdysone 26-hemiaceta; 1 diploclidine; 1 ecdysone; 1 ecdysone 3(2)-acetate 22-phosphate; ecdysone 3-acetate; ecdysone 22-acetate; 1 ecdysone 3-acetate 2-phosphate; 1 ecdysone 22-adenosine-monophosphate; 1 ecdysone 3-diacetate 22-phosphate; and/or ecdysone 22-glucoside.

In addition to the above, the disclosures contained within this document may yet further apply to ecdysteroids other than ecdysterone, such as by way of non-limiting example, the following ecdysteroids: 1 ecdysone 22-glycolate; ecdysone 22-linoleate; ecdysone 22-n6-(isopentenyl)-adenosine-monophosphate; ecdysone 25-o-β-d-glucopyranoside; ecdysone 3-o-β-d-glucopyranoside; ecdysone 22-oleate; ecdysone 22-palmitate; ecdysone 22-palmitoleate; ecdysone 22-phosphate; ecdysone 2-phosphate; ecdysone 3-phosphate; ecdysone 22-stearate; ecdysone 22-sulfate; ecdysonoic acid; ecdysteroside; 24-epi-abutasterone; 1 28-epi-cyasterone; 1 3-epi-cyasterone; 1 3-epi-cyasterone 22-acetate; 1 epicyasterone c 5-epi-cyasterone; 1 3-epi-22-deoxy-26-dihydroxyecdysone; 3-epi-22-deoxy-26-dihydroxyecdysone 2-phosphate; 3-epi-2-deoxyecdysone; 3-epi-2-deoxyecdysone 3-phosphate; 3-epi-2-deoxyecdysone 22-phosphate; 3-epi-2-deoxy-20-hydroxyecdysone; 3-epi-22-deoxy-20-hydroxyecdysone; 3-epi-22-deoxy-20-hydroxyecdysone 2-phosphate; 3-epi-22-deoxy-16B 20-dihydroxyecdysone; 3-epi-22-deoxy-16B 20-dihydroxyecdysone 2-phosphate; 3-epi-26-dihydroxyecdysone; 3-epi-ecdysone; 3-epi-ecdysone 22-phosphate; 25-ep 28-epi-cyasterone c 28-epi-isocyasterone; 3-epi-20-hydroxyecdysone; 3-epi-26-hydroxyecdysone; 14-epi-20-hydroxyecdysone; 22-epi-20-hydroxyecdysone; 3-epi-20-hydroxyecdysone 3-phosphate; 22-epi-14-hydroxypinnaster 2-acetate; 24-epi-makisterone a; 24-epi-pinnatasterone; 3-epi-poststerone; 4-epi-pterosterone; 3-epi-rubrosterone; 28-epi-sengosterone; 22-epoxy-1 25-terahydroxy-ergost-7-en-6-one polyporusterone; 26-epoxy-1 22-tetrahydroxy-ergost-7-en-6-one polyporusterone; 23-epoxy-1 24-tetrahydroxy-ergost-7-en-6-one polyporusterone j; ergosta-22-triene-6-dione; fibraurecdyside makisterone a 3-β-d-glucoside; gerardiasterone; gymnasterone b; herkesterone; 3β 14α 17α 25-hexahydroxy-5α-ergosta-22-dien-6-one; 5-hydroxyabutasterone; 14-hydroxyacetylpinnaster; and/or 25-hydroxyatrotosterone a.

The disclosures contained within this document may still further apply to ecdysteroids other than ecdysterone, such as by way of non-limiting example, the following ecdysteroids: 25-hydroxyatrotosterone b; 14-hydroxycarpester; 23-hydroxycyasterone; 24-hydroxycyasterone; 25-hydroxydacryhainansterone; 1-hydroxy-22-didehydrotaxisterone; 24-hydroxy-28-dihydrocarthamosterone; 20-hydroxyecdysone; 24-hydroxyecdysone; 26-hydroxyecdysone; 11α-hydroxyecdysone; 20-hydroxyecdysone 3(2)-acetate 22-phosphate; 20-hydroxyecdysone 3(2)-phosphate; (5α)-20-hydroxyecdysone epiecdysterone; 20-hydroxyecdysone 22-acetate; 20-hydroxyecdysone 2-acetate; 20-hydroxyecdysone 3-acetate; 20-hydroxyecdysone 3-acetate 2-phosphate; 20-hydroxyecdysone 20-benzoate; (5α)-20-hydroxyecdysone 22-benzoate; 20-hydroxyecdysone 22-benzoate; 20-hydroxyecdysone 22-benzoate 25-glucoside; 20-hydroxyecdysone 2-cinnamate; 20-hydroxyecdysone 2-β-d-glucopyranoside; 20-hydroxyecdysone 25-β-d-glucoside; 20-hydroxyecdysone 3-β-d-glucoside; 20-hydroxyecdysone 22-diacetate; 20-hydroxyecdysone 22-diacetate; 20-hydroxyecdysone 3; 22-diacetonide; 20-hydroxyecdysone 25-dibenzoate; 20-hydroxyecdysone 22-ethylidene; 26-hydroxyecdysone 22-glucoside; 20-hydroxyecdysone 22-glycolate; 20-hydroxyecdysone 22-linoleate; 20-hydroxyecdysone 22-monoacetonide; 20-hydroxyecdysone 3-monoacetonide; 20-hydroxyecdysone 22-oleate; 240 20-hydroxyecdysone 22-palmitate; 20-hydroxyecdysone 3-p-coumarate; 26-hydroxyecdysone 26-phosphate; 20-hydroxyecdysone 22-phosphate; 26-hydroxyecdysone 2-phosphate; 20-hydroxyecdysone 22-stearate; 20-hydroxyecdysonoic acid; (24r)-24-(2-hydroxyethyl)-20-hydroxyecdysone; 20-hydroxy-24-hydroxymethylecdysone; 25-hydroxypanuosterone; 250 14-hydroxypinnaster; 14-hydroxypinnaster 3-acetate; 26-hydroxypinnatasterone; 26-hydroxypolypodine b; and/or 11a-hydroxypoststerone.

Additionally, the disclosures contained within this document may yet further apply to ecdysteroids other than ecdysterone, such as by way of non-limiting example, the following ecdysteroids: 11α-hydroxyrubrosterone; 5β-hydroxyrubrosterone; hyousterone a; hyousterone b; hyousterone c; hyousterone d; inokosterone; callinecdysone a; inokosterone 26-acetate; inokosterone 22-acetonide; integristerone a; integristerone a 25-acetate; integristerone b; isocyasterone c; 25-epi-cyasterone; isocyasterone 3-monoacetonide; isovitexirone; kaladasterone; kancollosterone; lesterone; leuzeasterone; limnantheoside a; limnantheoside b; limnantheoside c; makisterone a; makisterone b; makisterone c; podecdysone a; lemmasterone; makisterone d; malacosterone; melandrioside a; 24-methyleneshidasterone; 24-methylshidasterone; muristerone a; 29-norcyasterone; 29-norcyasterone 2-acetate; 29-norcyasterone 3-acetate; 29-norsengosterone; nusilsterone; osladin; 22-oxocyasterone; 22-oxo-20-hydroxyecdysone; palythoalone a; palythoalone b; panuosterone; paristerone; paxillosterone; paxillosterone 22-p-hydroxybenzylidene aceta; 300 2β 3α 6α 25-pentahydroxy-5b-cholestane; 2β 3β 6α 25-pentahydroxy-5b-cholestane; pinnaster; pinnatasterone; podecdysone b; podecdysone b 25-o-β-d-glucoside; polypodine b; (5α)-polypodine b; polypodine b 22-acetate; polypodine b 22-acetonide; polypodine b 22-benzoate; polypodine b 2-cinnamate; polypodine b 3β-d-glucoside; (5α)-polypodine b 3-β-d-glucoside; polypodoaurein; polypodogenin; polypodosaponin; polypodoside a; polypodoside b; polypodoside c; polyporusterone a; polyporusterone b; polyporusterone c; polyporusterone d; polyporusterone e; polyporusterone; polyporusterone; ponasterone a; ponasterone a 22-glycolate; ponasterone b; ponasterone c; ponasterone c 2-cinnamate; ponasteroside a; poststerone; praemixisterone; precyasterone; pterosterone; pterosterone 3-o-β-d-glucopyranoside; and/or pterosterone 24-o-β-d-glucoside.

Finally, the disclosures contained within this document may apply to ecdysteroids other than ecdysterone, such as by way of non.-limiting example, the following ecdysteroids: rapisterone; rapisterone b; rapisterone c; rapisterone d; rapisterone d 20-acetate; reptansterone; rhapontisterone punisterone; rhapontisterone; rubrosterone; scabrasterone; schizaeasterone a; schizaeasterone b; sengosterone; serfurosterone a; serfurosterone b; shidasterone; stachysterone d; sidasterone a; sidasterone b; sidisterone; sileneoside a; sileneoside b; sileneoside c; sileneoside d; sileneoside; sileneoside; sileneoside; (5α)-silenoside e; silenosterone 3-dehydro-2-deoxyecdysone; sogdisterone; stachysterone a; stachysterone b; stachysterone b 1 15-epoxide; stachysterone c; taxisterone; tenuifolioside a; tenuifolioside b; 25-tetradeoxyecdysone; 3β 5α 9α 14α-tetrahydroxyergosta-22(e)-dien-6-one; tomentesterone a; tomentesterone b; 25-trideoxyecdysone; trihydroxyecdysone; trihydroxyergosta-22-dien-6-one; trihydroxyergosta-22(e)-dien-6-one; turkesterone; venustone; viperidinone; viperidone; vitexirone; and/or viticosterone e, including any possible esters and salts of the foregoing, consistent with these disclosures.

Known ecdysteroids and/or ecdysteroid compounds may have one or more of the following effects: increasing body protein synthesis; amelioration of psychological depression; enhancement of immune system; stimulation of carbohydrate metabolism; reduction of cholesterol levels; enhancement of liver function; restoration of urea balance; amelioration of renal dysfunction; reduction of DNA damage; enhancement of wound healing; cardiovascular system health; increasing antibiotic and antiviral activity; increasing antioxidant and anti-aging activity; resistance of arrhythmia; increased personal energy; and/or enhancement of male sexual potency.

Notwithstanding the wide variety of possible beneficial effects possessed by ecdysteroids generally, ecdysteroids may nevertheless possess short half-lives and may be poorly distributed in muscle tissue. Significantly, the low distribution of ecdysteroids in skeletal muscle tissue may limit their effects for athletic purposes, especially since the effects of ecdysteroids are typically concentration-dependent. The largest concentrations of ecdysteroids are typically located in the human liver and the kidneys, respectively. In addition, ecdysteroids are typically metabolized rapidly and are excreted through bile and urine. In addition to being rapidly metabolized, ecdysteroids typically tend to be very hydrophilic molecules, and therefore their urine excretion may be further increased.

The applicants have discovered that the effectiveness of oral administration of ecdysteroids on humans may be increased by, among other things, providing greater bioavailability, longer half life, and/or improved distribution of ecdysteroids to skeletal muscle tissue.

One particular example of an ecdysteroid is ecdysterone. Ecdysterone is presently used in the dietary supplement industry to supplement naturally-occurring Ecdysterone production in the body. Various supplemental ecdysterone forms are presently available in the consumer marketplace. Nevertheless, many commercially-available ecdysterone forms may possess poor bioavailability, short half-lives, and/or may be poorly distributed in skeletal muscle tissue. In addition to the other particular implementations of ecdysterone compounds described and made possible herein, edcysterone decanoate and ecdysterone isobutyrate are first and second particular implementations, respectively, of novel ecdysterone compounds (and methods of manufacture and use thereof) that, with respect to the human administration of ecdysterone, may increase bioavailability, half life and distribution to skeletal muscle tissue. As set forth at length below, ecdysterone decanoate may comprise ecdysterone (and/or any pharmacologically active salts or esters thereof) in compound with decanoic acid (and/or one or more decanoates). In addition, as described further below, ecdysterone isobutyrate may comprise ecdysterone (and/or any pharmacologically active salts or esters thereof) in compound with isobutyric acid (and/or one or more isobutyrates).

Particular implementations of ecdysterone compounds may further comprise esters of ecdysterone at the 2-OH group and/or other hydroxyl groups which may likewise be beneficial in increasing bioavailability, half-life and distribution to skeletal muscle tissue in humans. Accordingly, particular implementations of ecdysterone compounds may comprise any ester or salt of ecdysterone in compound with one of decanoic acid (and/or one or more decanoates) and isobutylic acid (and/or one or more isobutyrates). Various ecdysterone esters, mainly acetates, exist in nature, although such esters may comprise only a small percentage of a given plant's total ecdysterone content. By way of non-limiting example, some natural acetates include: AJUGALIDE E [cf. 2-EPI-CYASTERONE 22-ACETATE]; CYASTERONE 22-ACETATE; CYASTERONE 3-ACETATE; 2-DEOXYECDYSONE 22-ACETATE; 2-DEOXYECDYSONE 3-ACETATE; 2-DEOXY-20-HYDROXYECDYSONE 22-ACETATE; 2-DEOXY-20-HYDROXYECDYSONE 3-ACETATE; (5α)-2-DEOXY-20-HYDROXYECDYSONE 3-ACETATE; 2-DEOXY-20-HYDROXYECDYSONE 25-ACETATE; 2-DEOXY-20-HYDROXYECDYSONE 3,22-DIACETATE; 20,26-DIHYDROXYECDYSONE 22-ACETATE; 20,26-DIHYDROXYECDYSONE 2,22-DIACETATE; 20,26-DIHYDROXYECDYSONE 3,22-DIACETATE; ECDYSONE 3(/2)-ACETATE 22-PHOSPHATE; ECDYSONE 3-ACETATE; ECDYSONE 22-ACETATE; ECDYSONE 3-ACETATE 2-PHOSPHATE; ECDYSONE 2,3-DIACETATE 22-PHOSPHATE; 3-EPI-CYASTERONE 22-ACETATE;

22-EPI-14-HYDROXYPINNASTEROL 2-ACETATE; 20-HYDROXYECDYSONE 3(/2)-ACETATE 22-PHOSPHATE; 20-HYDROXYECDYSONE 22-ACETATE; 20-HYDROXYECDYSONE 2-ACETATE; 20-HYDROXYECDYSONE 3-ACETATE; 20-HYDROXYECDYSONE 3-ACETATE 2-PHOSPHATE; 20-HYDROXYECDYSONE 3,22-DIACETATE; 20-HYDROXYECDYSONE 2,22-DIACETATE; 14-HYDROXYPINNASTEROL 3-ACETATE; INOKOSTERONE 26-ACETATE; INTEGRISTERONE A 25-ACETATE; 29-NORCYASTERONE 2-ACETATE; 29-NORCYASTERONE 3-ACETATE; POLYPODINE B 22-ACETATE, and/or; RAPISTERONE D 20-ACETATE.

Some primary esterification sites in nature may include the 2, 3, 22 and 23 carbon-molecules. Notwithstanding, in the presence of appropriate strong esterification conditions, such as those created in a laboratory setting, each and every —OH (hydroxyl) group could potentially be esterified, thus providing molecules with as many (or as few) as 5, 6, or more esterified —OH groups. Alternatively, and in addition to the foregoing, particular implementations of ecdysterone compounds may comprise any of the various compounds (and/or salts or esters thereof) set forth in this document, in compound with one of decanoic acid (and/or one or more decanoates) and/or isobutyric acid (and/or one or more isobutyrates). In other alternative implementations, organic acids such as, by way of non-limiting example, acetic acid, isobutilic acid, propionic acid, decanoic acid, formic acid, butylic acid, pantanoic acid, benzoin acid, fumaric acid, malic acid, citric acid, tartaric acid and/or various other organic acids may be used to esterify the hydroxyl groups. In addition to the foregoing, many additional ecdysterone compounds are possible.

The foregoing and the following particular implementations of ecdysterone compounds, and other particular implementations made possible with the disclosures contained herein, may be particularly useful in providing the effects of single-administration ecdysterone and various known ecdysterone compounds, while desirably increasing the bioavailability, half life and distribution to skeletal muscle tissue of ecdysterone in humans.

Referring now specifically to ecdysterone, this molecule comprises the basic formula:

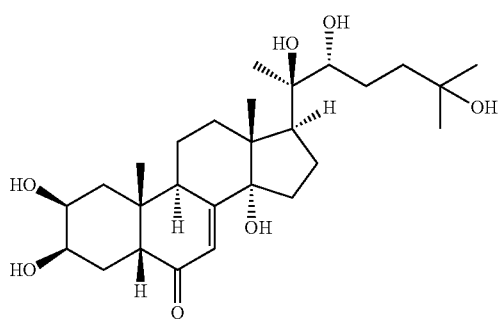

The principal metabolites of ecdysterone are 2-deoxyecdysone (metabolite II) and deoxyecdysone (metabolite III). Significantly, the —OH group at the second carbon molecule is particularly important for ecdysteroid anabolic activity. Accordingly, the 2-deoxyecdysone metabolite may be particularly inactive. By way of non-limiting example, some characteristics for high anabolic activity may include: a complete sterol side-chain; a 22R oxygen function, and containing, in some cases, additional alkyl groups at the 24a-position; an oxygen function generally in the form of a 3b-OH group; additional —OH groups at C-14a and C-2b, and, in many cases, also at C-20 and C-25. In addition to the foregoing, 2-acetyl derivatives and/or 25-benzoate derivatives of 20E may comprise a significant amount of anabolic activity. Nevertheless, some di-esters and some tri-esters of ecdysterone, as well as many glucosidic derivatives of 20E, may be much less anabolically active (or even virtually inactive) relative to 20E. In addition to the foregoing, the presence of a 2,3-diol system may play a significant role in the manifestation of anabolic effects of 20E.

Referring now to decanoic acid, this molecule comprises the basic formula:

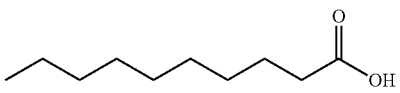

Decanoic acid, alternatively known as capric acid, is a saturated fatty acid comprising the formula $CH_3(CH_2)_8COOH$. Salts and esters of decanoic acid are collectively called decanoates. As described further herein, various decanoates may be used in conjunction with ecdysterone (or esters thereof) to form particular implementations of ecdysterone compounds in order to at least increase the bioavailability, half life and distribution to skeletal muscle tissue of ecdysterone in humans. Of course, since decanoic acid is a saturated fatty acid, it may not contain any double bonds or other functional groups along the chain. Also, significantly, all carbons (apart from the carboxylic acid —COOH group) contain a full complement of hydrogen atoms. This is significant because, as shown above, decanoic acid molecules may form a relatively straight chain and, as a result, can be packed together very tightly.

Turning now to isobutyric acid, this molecule comprises the basic formula:

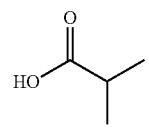

Isobutyric acid, also known as 2-methylpropanoic acid, is a carboxylic acid with the structural formula $(CH_3)_2$—CH—COOH. For the purposes of this disclosure, salts and esters of isobutyric acid are collectively called isobutyrates. Non-limiting examples of isobutyrates include sodium isobutyrate and/or potassium isobutyrate. As described further herein, various isobutyrates may be used in conjunction with ecdysterone (or esters thereof) to form particular implementations of ecdysterone compounds. Of course, isobutyric acid is an isomer of n-butyric acid, meaning the compositions have the same chemical formula, $C_4H_8O_2$ (but a different structure). Isobutyric acid may be alternatively prepared at least via: the hydrolysis of isobutyronitrile with alkalis; via the oxidation of isobutanol with potassium dichromate and sulfuric acid; and/or via the action of sodium amalgam on methacrylic acid.

TERMINOLOGY AND DEFINITIONS

In describing particular implementations of ecdysterone compounds, the following terminology will be used in accordance with the definitions and explanations set out below.

Notwithstanding, other terminology, definitions, and explanations may additionally be found throughout this document.

As used herein, "ecdysterone" is a term used in its broadest sense and may refer to ecdysterone in its many different chemical forms, including single administration ecdysterone, its physiologically active salts or esters, its combinations with its various salts, its tautomeric, polymeric and/or isomeric forms, its analog forms, and/or its derivative forms.

As used herein, "compound" is a term used in its broadest sense and may refer to an ecdysteroid in combination with one of decanoic acid (and/or one or more decanoates) and isobutyric acid (and/or one or more isobutyrates).

As used herein, "decanoic acid" is a term used in its broadest sense and may refer to a saturated fatty acid comprising the formula $CH_3(CH_2)_8COOH$, in its many different chemical forms, including single administration decanoic acid, its physiologically active salts or esters, its combinations with its various salts, its tautomeric, polymeric and/or isomeric forms, its analog forms, its derivative forms, and/or its decarboxylation products.

As used herein, "decanoate(s)" is a term used in its broadest sense and may refer to the various salts and esters of decanoic acid in their many different chemical forms including one or more single administration decanoates, their physiologically active salts or esters, their combinations with its various salts, their tautomeric, polymeric and/or isomeric forms, their analog forms, their derivative forms, and/or their decarboxylation products.

As used herein, "isobutyric acid" is a term used in its broadest sense and may refer to a carboxylic acid with the structural formula $(CH_3)_2$—CH—COOH in its many different chemical forms, including single administration isobutyric acid, its physiologically active salts or esters, its combinations with its various salts, its tautomeric, polymeric and/or isomeric forms, its analog forms, its derivative forms, and/or its decarboxylation products.

As used herein, "isobutyrate(s)" is a term used in its broadest sense and may refer to the various salts and esters of isobutyric acid in their many different chemical forms including one or more single administration decanoates, their physiologically active salts or esters, their combinations with its various salts, their tautomeric, polymeric and/or isomeric forms, their analog forms, their derivative forms, and/or their decarboxylation products.

As used herein, "pharmaceutically acceptable additive" or "additive" are terms used in their broadest sense. Particular implementations of the compositions described in this document may also comprise an additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof). These additives may be solids or liquids, and the type of additive may be generally chosen based on the type of administration being used. Those of ordinary skill in the art will be able to readily select suitable pharmaceutically effective additives from the disclosure in this document. In particular implementations, pharmaceutically acceptable additives may include, by non-limiting example, calcium phosphate, cellulose, stearic acid, croscarmelose cellulose, magnesium stearate, and silicon dioxide.

As used in this document, "pharmaceutically effective" is a phrase used in its broadest sense, including, by non-limiting example, effective in a clinical trial, for a specific patient, or only placebo-effective.

As used in this document, "pharmaceutically acceptable" is a phrase used in its broadest sense and may describe ingredients of a pharmaceutical composition that meet Food and Drug Administration (FDA) standards, United States Pharmacopeial Standards (USP), US Department of Agriculture (USDA) standards for food-grade materials, commonly accepted standards of the nutritional supplement industry, industry standards, botanical standards, or standards established by any individual. These standards may delineate acceptable ranges of aspects of ingredients of a pharmaceutical composition such as edibility, toxicity, pharmacological effect, or any other aspect of a chemical, composition, or preparation used in implementations of a pharmaceutical composition.

Compounds/Components

A first particular implementation of an ecdysterone compound is ecdysterone decanoate of the formula:

$$[X]\cdot Y$$

wherein;

X is the ecdysterone group identified and defined above; and
Y is decanoic acid.

The first particular implementation of ecdysterone compound, ecdysterone decanoate, may be synthesized using the disclosures contained herein, according to many common processes and procedures known in the art, and using known materials and equipment. In addition, other particular implementations of ecdysterone compounds described below, such as, by way of non-limiting example, ecdysterone isobutyrate and/or other ecdysterone compounds described and/or made possible herein, may likewise be synthesized in accordance with these disclosures. With respect to any of the ecdysterone compounds disclosed herein, a method for isolation and/or synthesis thereof may begin with the isolation of ecdysterone.

The extraction and/or isolation of various ecdysteroids (including ecdysterone) from dried plant material may require relatively large volume of a polar solvent, such as methanol. In some particular implementations, plant material may be saturated with methanol (thus forming a methanolic solution). In such particular implementations, a solvent-plant ratio may be about 10:1, although other ratio ranges may be effectively used. Various stages of isolation/purification of ecdysterone may exist, according to the particular implementation being used. By way of non-limiting example, various stages may include one or more of the following: solvent stage; pre-purification stage; precipitation stage; washing stage; evaporation stage; dissolution stage; separation stage; elution stage; adsorption stage; chromatographic stage; purification stage; and/or resolution stage. It will be understood that additional stages and sub-stages may likewise be provided, and that one or more of the foregoing stages may be combined with one or more other stages to form a single compound stage. In addition, it will be further understood that one, all, or some of the stages described above may be provided and/or performed with respect to any particular implementation of ecdysterone compound described or made possible herein.

One non-limiting example of a pre-purification stage involves using a charged-based batch separation. A pre-purification stage, in this particular implementation, may further involve one or more of: fractionated precipitation; solvent-solvent distribution; and/or a hybrid chromatographic method known in the relevant art. A fractionated precipitation may be performed repeatedly as desire and/or required. In some particular implementations, a fractioned precipitation may be performed between one and five times (three times, in some particular implementations). Notwithstanding, in other particular implementations, a fractioned precipitation may be performed either greater or fewer than one and/or five times. In any event, the methanolic solution may be mixed with a half amount, having the same volume, and with a doubled volume of acetone. After each precipitation step, the solution may increasingly include ecdysteroids. The precipitate may be further washed with the same ratio of methanol and acetone. Significantly, the washing solution may also be combined with the methanolic solution. After combination, the solutions may be evaporated, further dissolved in methanol, and thereafter subjected to acetone precipitation. After acetone precipitation, the solution may be taken into dryness, and further dissolved in 50% aqueous methanol.

The solvent-solvent distribution described above may be performed between aqueous methanol and hexane, in particular implementations. Significantly, any ecdysteroids present may be located in the aqueous methanol (bottom) phase. After separating the respective phases, the bottom phase may be evaporated and the residue may be thereafter dissolved in plain methanol. The methanolic solution may thereafter be mixed with aluminum oxide, and the suspension may be taken into dryness in a rotary evaporator. The sample-stationary phase ratio may be small (1:2), and may result in the removal of a number of contaminants, while resulting in the concomitant purification of any ecdysteroids.

Elution of ecdysterone may be further carried out using various volume ratios of dichloromethane and ethanol (96%), such as, by way of non-limiting example, 95:5, 9:1, 8:2 and/or 1:1. Various ecdysteroids of interest may be eluted with dichloromethane-ethanol (96%) (9:1 and 8:2), although other compounds and/or concentrations may likewise be used. The eventual separation of ecdysterone compounds is based on adsorption/desorption processes of alumina. Because of the strong interaction between the matrix components and the adsorbent, an abundant amount of contaminant may be retarded on the adsorbent (aluminum oxide, in this particular implementation), thus allowing the ecdysteroids to be selectively eluted with an appropriate mobile phase(s). Accordingly, it will be understood that the adsorption of certain ecdysteroids to the adsorbent may be reduced using a water-containing eluent. Notwithstanding the above-described adsorption, the single employment of aluminum oxide stationary phase may be necessary at least once, in those particular implementations where a high sample load (e.g. a 200 gram sample with respect to 400 grams of aluminum oxide) is used. Thus, various ecdysterone compounds may use a gradient elution in column chromatography. In such particular implementations, approximately four gradient steps may be used. Of course, depending upon the particular implementation being used, either a greater or fewer number than four gradient steps may be used. It will be understood that the gradient steps are particularly useful in providing coarse separation according to the adsorption ability of various ecdysteroids.

One or more of the pre-purification stages described above may be followed by single or repeated liquid adsorption chromatography. The various aspects relating to the method disclosed herein with respect to this particular implementation may allow for ecdysterone separation according to the relative partition and lipophilicity of the various ecdysteroids. In some particular implementations, elution may be carried out with various mixtures of aqueous methanol, using stepwise gradient elution with a 5% increase of the methanol content in each successive step. Various ecdysteroids of interest may then be eluted in the following non-limiting exemplary elution order: integristerone A; 20-hydroxyecdysone; 5α-20-hydroxyecdysone; 5α-2-deoxyintegristerone A; 2-deoxy-20-hydroxyecdysone 22-O-β-D-glucopyranoside; 22-deoxyintegristerone A; polypodine B; 24(28)-dehydromakisterone A; 9α,20-dihydroxyecdysone; 2-deoxypolypodine B; 2-deoxy-20-hydroxyecdysone; and 22-deoxy-20-hydroxyecdysone, using 35-40%, 40-45% and 50-60% aqueous methanol, respectively.

It will be understood that it is at least the organic modifier (methanol, in this particular implementation) content of the mobile phase that may enable the dissolution of the octadecyl silica stationary phase that may be provided with the eluent. It should be noted that the reversed-phase stationary phase may be versatile, the column may be reusable, and may be operated at low pressure (less than 1 atmosphere, in some particular implementations). In the particular implementation described above, the mobile phase flow may be generated by the use of vacuum at a column outlet. Nevertheless, the mobile phase flow may be accomplished using other techniques known in the relevant art. It will be appreciated that various aqueous-methanol mixtures can easily regenerate the stationary phase described above. In this particular implementation, the particle size of the stationary phase may be between 60-200 μm (microns), and the whole procedure was carried out at a low-pressure drop (e.g. less than 1 atmosphere).

Significantly, not each and every known ecdysteroid/ecdysteroid compound may be isolatable according to the disclosures set forth above. It will be understood by those having ordinary skill in the art that co-eluted compounds may be resolved either by repeated use of the same low-pressure reversed-phase chromatographic column, or with an additional use of either high-performance liquid chromatography (HPLC) or preparative thin-layer chromatography (TLC). Significantly, normal phase HPLC may provide adequate separation.

It will be understood that the first steps of isolation set forth above targets the 20-hydroxyecdysone, a major phytoecdysteroid. It will be further understood that the various ecdysterone compounds disclosed herein including, by way of non-limiting example, ecdysterone decanoate and/or ecdysterone isobutyrate, may be manufactured and/or synthesized using the foregoing techniques to isolate ecdysterone in addition to other techniques set forth below.

Significantly, in some particular implementations, synthesizing ecdysterone decanoate and/or ecdysterone isobutyrate (and/or other ecdysterone compounds made possible with these disclosures) from 20-hydroxyecdysone may comprise using known enzymatic reactions. In other particular implementations, synthesizing ecdysterone decanoate and/or ecdysterone isobutyrate (and/or other ecdysterone compounds made possible with these disclosures) may comprise adding an amide group (or other functional group) using ammonia ($NH_3$) under high-pressure conditions (greater than 1 atmosphere, in some particular implementations), or by another known technique for amidization.

In some particular implementations, as described herein, any pharmacologically active salt or ester of ecdysterone may be used to form an ecdysterone compound. In addition, as set forth above, some particular implementations of ecdysterone compounds may comprise one or more esters of ecdysterone at the 2-OH group (and/or other hydroxyl groups). Also, with respect to any of the foregoing implementations, one or more decanoates (salts and/or esters of decanoic acid) may be added in combination with one or more ecdysteroids. Thus, synthesizing ecdysterone decanoate from raw 20E may comprise various techniques as set forth herein including, by way of non-limiting example, the amidization of ecdysterone with various decanoates. While particular sequences or steps have been described above, it will be understood that such description is not limited to the specific order of steps or forms as disclosed. Any steps or sequences of steps of manufacture of particular implementations of ecdysterone compounds in any form are given as examples of possible steps or sequences of steps or potential forms and not as limitations, since many possible manufacturing processes and sequences of steps may be used to manufacture particular implementations of ecdysterone compounds in a wide variety of forms, consistent with the disclosures contained herein.

A second particular implementation of an ecdysterone compound is ecdysterone isobutyrate of the formula:

$$[X]\cdot Y$$

wherein;
X is the ecdysterone group identified and defined above; and
Y is isobutyric acid.

With respect to the second particular implementation of ecdysterone compound, Applicants have synthesized ecdysterone isobutyrate at least via the following exemplary method.

In some particular implementations, as described herein, any pharmacologically active salt or ester of ecdysterone may be used. Specifically, as set for the above, some particular implementations of ecdysterone compounds may comprise one or more esters of ecdysterone at the 2-OH group and/or other hydroxyl groups.

In some particular implementations, as described herein, any pharmacologically active salt or ester of ecdysterone may be used to form an ecdysterone compound. In addition, as set forth more at length below, some particular implementations of ecdysterone compounds may comprise one or more esters of ecdysterone at the 2-OH group (and/or other hydroxyl groups). Also, with respect to any of the foregoing implementations, one or more isobutyrates (salts and/or esters of isobutyric acid) may be added in combination with one or more ecdysteroids. Thus, synthesizing ecdysterone isobutyrate from raw 20E may comprise various techniques as set forth herein including, by way of non-limiting example, the amidization of ecdysterone with various isobutyrates.

The various ecdysterone compounds, compositions and/or formulations according to the present document, including the various ecdysterone decanoates and ecdysterone isobutyrates made possible with these disclosures, may be administered in any form, including one of a capsule, a cachet, a pill, a tablet, a powder, a granule, a pellet, a bead, a particle, a troche, a lozenge, a pastille, a solution, an elixir, a syrup, a tincture, a suspension, an emulsion, a mouthwash, a spray, a drop, an ointment, a cream, a gel, a paste, a transdermal patch, a suppository, a pessary, cream, a gel, a paste, a foam, and combinations thereof for example. Compositions and/or formulations of the present document may also include a acceptable additive (e.g. one of a solubilizer, an enzyme inhibiting agent, an anticoagulant, an antifoaming agent, an antioxidant, a coloring agent, a coolant, a cryoprotectant, a hydrogen bonding agent, a flavoring agent, a plasticizer, a preservative, a sweetener, a thickener, and combinations thereof) and/or a acceptable carrier (e.g. one of an excipient, a lubricant, a binder, a disintegrator, a diluent, an extender, a solvent, a suspending agent, a dissolution aid, an isotonization agent, a buffering agent, a soothing agent, an amphipathic lipid delivery system, and combinations thereof).

Implementations of ecdysterone compounds may further be synthesized or created in a wide variety of manners, and may be made from a wide variety of materials. From these disclosures, those of ordinary skill in the art will readily be able to select appropriate materials and methods to manufacture and use the compounds disclosed herein.

Dosage Forms

Implementations of ecdysterone compounds may conveniently be presented in unit dosage form. Unit dosage formulations may be those containing a daily dose or unit, a daily sub-dose, or an appropriate fraction thereof, of the administered components as described herein.

A dosage unit may include an ecdysterone compound. In addition, a dosage unit may include an ecdysterone compound admixed with a pharmaceutically acceptable additive(s), and/or any combination thereof.

The dosage units may be in a form suitable for administration by standard routes. In general, the dosage units may be administered, by non-limiting example, by the topical (including buccal and sublingual), transdermal, oral, rectal, ophthalmic (including intravitreal or intracameral), nasal, vaginal, and/or parenteral (including subcutaneous, intramuscular, intravenous, intradermal, intratracheal, and epidural) routes.

For the exemplary purposes of this disclosure, oral delivery may be a particularly advantageous delivery route for administration to humans and animals of implementations of a pharmaceutical composition, optionally formulated with appropriate pharmaceutically acceptable additives to facilitate administration.

Manufacture

Particular implementations of ecdysterone compounds may be made using conventional or other procedures. Accordingly, although there are a variety of method implementations for producing pharmaceutical compositions, for the exemplary purposes of this disclosure, various exemplary non-limiting method implementations for producing an ecdysterone compound has been set forth above.

Measuring specific quantities of and pharmaceutically acceptable additives or inert ingredients, may involve any number of steps and implementing components, and measuring specific quantities of ecdysteroids (including their physiologically active salts or esters), ecdysterone (including its physiologically active salts or esters); decanoic acid, one or more decanoates, isobutyric acid, one or more isobutyrates, and pharmaceutically acceptable additives or inert ingredients, may be accomplished readily from this disclosure. For the exemplary purposes of this disclosure, measuring specific quantities of ecdysteroids, ecdysterone; decanoic acid, one or more decanoates, isobutyric acid, one or more isobutyrates, and pharmaceutically acceptable additives or inert ingredients, may comprise using a scale, a solid or liquid dispensing apparatus, or other measurement device capable of measuring solid mass or liquid volume to produce a desired quantity of ecdysteroids, ecdysterone; decanoic acid, one or more decanoates, isobutyric acid, one or more isobutyrates, and/or pharmaceutically acceptable ingredient.

It should be appreciated that any of the components of particular implementations of an ecdysterone compound may be used as supplied commercially, or may be preprocessed by, by non-limiting example, any of the methods and techniques of agglomeration, air suspension chilling, air suspension drying, balling, coacervation, comminution, compression, pelletization, cryopelletization, extrusion, granulation, homogenization, inclusion compoundation, lyophilization, melting, mixed, molding, pan coating, solvent dehydration, sonication, spheronization, spray chilling, spray congealing, spray drying, or other processes known in the art depending in part on the dosage form desired. The various components may also be pre-coated or encapsulated as known in the art. It will also be clear to one of ordinary skill in the art that appropriate additives may also be introduced to the composition or during the processes to facilitate the preparation of the dosage forms, depending on the need of the individual process.

Mixing the measured quantities of ecdysteroids, ecdysterone, decanoic acid, one or more decanoates, isobutyric acid, and/or one or more isobutyrates, and pharmaceutically acceptable additives or inert ingredients, may involve any number of steps and implementing components, and may be accomplished readily from this disclosure. For the exemplary purposes of this disclosure, mixing the measured quantities of ecdysteroids, ecdysterone; decanoic acid, one or more decanoates, isobutyric acid, and/or one or more isobutyrates, and pharmaceutically acceptable additives or inert ingredients, may comprise combining the measured quantities of ecdysteroids, ecdysterone; decanoic acid, one or more decanoates, isobutyric acid, and/or one or more isobutyrates, and pharmaceutically acceptable additives or inert ingredients, under the influence of physical, ultrasonic, or electrostatic forces to create a desired degree of intermingling and/or chemical reaction of the ecdysteroids, ecdysterone; decanoic acid, one or more decanoates, isobutyric acid, and/or one or more isobutyrates and any pharmaceutically acceptable ingredients. The mixed may be accomplished when the ecdysteroids, ecdysterone; decanoic acid, one or more decanoates, isobutyric acid, and/or one or more isobutyrates and/or any pharmaceutically acceptable ingredients are in a solid, liquid, or semisolid state.

Separating the various particular implementations of ecdysterone compounds described herein into discrete quantities for distribution may involve any number of steps and implementing components, and separating the various particular implementations of ecdysterone compounds into discrete quantities for distribution may be accomplished readily from this disclosure. For the exemplary purposes of this disclosure, separating the various particular implementations of ecdysterone compounds into discrete quantities for distribution may involve utilizing a specific piece of equipment, for example, a conventional tablet forming apparatus to shape the formed composition into individual tablets, each containing a desired dose of the various implementations of ecdysterone compounds described herein. The separating process may be accomplished when the particular implementation of ecdysterone compound is in a solid, liquid, or semisolid state.

Those having ordinary skill in the art will be able to readily select manufacturing equipment and pharmaceutically acceptable additives or inert ingredients in order to readily manufacture particular implementations of ecdysterone compounds. For the exemplary purposes of this disclosure, some examples of pharmaceutically acceptable additives or inert ingredients and manufacturing process are included below, particularly those that relate to manufacture of the particular implementations of ecdysterone compounds in tablet form. Notwithstanding the specific examples given, it will be understood that those of ordinary skill in the art will readily appreciate how to manufacture various particular implementations of ecdysterone compounds according to the other methods of administration and delivery disclosed in this document.

Particular implementations of ecdysterone compounds may include a lubricant. Lubricants are any anti-sticking agents, glidants, flow promoters, and the like materials that perform a number of functions in tablet manufacture, for example, such as improving the rate of flow of the tablet granulation, preventing adhesion of the tablet material to the surface of the dies and punches, reducing interparticle friction, and facilitating the ejection of the tablets from the die cavity. Lubricants may comprise, for example, magnesium stearate, calcium stearate, talc, and colloidal silica.

Particular implementations of ecdysterone compounds may also include a binder. Binders are any agents used to impart cohesive qualities to powdered material through particle-particle bonding. Binders may include, for example, matrix binders (e.g. dry starch, dry sugars), film binders (e.g. celluloses, bentonite, sucrose), and chemical binders (e.g. polymeric cellulose derivatives, such as methyl cellulose, carboxy methyl cellulose, and hydroxy propyl cellulose); and other sugar, gelatin, non-cellulosic binders and the like.

Disintegrators may further be used in particular implementations of ecdysterone compounds to facilitate the breakup or disintegration of tablets after administration. Disintegrators may include, for example, starch, starch derivatives, clays (e.g. bentonite), algins, gums (e.g. guar gum), cellulose, cellulose derivatives (e.g. methyl cellulose, carboxymethyl cellulose), croscarmellose sodium, croscarmellose cellulose, and other organic and inorganic materials.

Particular implementations of ecdysterone compounds may still further include diluents, or any inert substances added to increase the bulk of an ecdysterone compound to make a tablet a practical size for compression. Diluents may include, for example, calcium phosphate, calcium sulfate, lactose, mannitol, magnesium stearate, potassium chloride, and citric acid, among other organic and inorganic materials.

Buffering agents may also be included in particular implementations of ecdysterone compounds and may be any one of an acid and a base, where the acid is, for example, propionic acid, p-toluenesulfonic acid, salicylic acid, stearic acid, succinic acid, tannic acid, tartaric acid, thioglycolic acid, or toluenesulfonic acid, and the base is, for example, ammonium hydroxide, potassium hydroxide, sodium hydroxide, sodium hydrogen carbonate, aluminum hydroxide, calcium carbonate, and other organic and inorganic chemicals.

Particular implementations of ecdysterone compounds may also be administered through use of amphipathic lipid delivery systems (such as liposomes and unilamellar vesicles), caplet systems, oral liquid systems, parenteral and/or intravenous systems, topical systems (creams, gels, transdermal patches, etc.), intranasal systems, rectal or vaginal systems, and many other delivery methods and/or systems known to those of ordinary skill in the art. Those of ordinary skill in the art will readily be able to select additional pharmaceutically acceptable additives to enable delivery of implementations of a pharmaceutical composition from the disclosure in this document.

With respect to delivery of particular implementations of the particular implementations of ecdysterone compounds described and made possible herein, and for the exemplary purposes of this disclosure, tablets may be utilized. Tablets are any solid pharmaceutical dosage form containing a pharmaceutically acceptable active agent or agents to be administered with or without suitable pharmaceutically acceptable additives and prepared either by compression or molding methods well known in the art. Tablets have been in widespread use and remain popular as a dosage form because of the advantages afforded both to the manufacturer (e.g., simplicity and economy of preparation, stability, and convenience in packaging, shipping, and dispensing) and the patient (e.g., accuracy of dosage, compactness, portability, blandness of taste, and ease of administration). Although tablets are most frequently discoid in shape, they may also be round, oval, oblong, cylindrical, rectangular or triangular, for example. The tablets may be optionally scored so that they may be separated into different dosages. They may differ greatly in size and weight depending on the amount of the pharmaceutically acceptable active agent or agents present and the intended route of administration. Tablets are typically divided into two general classes, (1) compressed tablets, and (2) molded tablets.

Tablets and other orally discrete dosage forms, such as capsules, cachets, pills, granules, pellets, beads, and particles, for example, may optionally be coated with one or more enteric coatings, seal coatings, film coatings, barrier coatings, compress coatings, fast disintegrating coatings, or enzyme degradable coatings for example. Multiple coatings may be applied for desired performance. Further, dosage forms may be designed for, by non-limiting example, immediate release, pulsatile release, controlled release, extended release, delayed release, targeted release, synchronized release, or targeted delayed release. For release/absorption control, carriers may be made of various component types and levels or thicknesses of coats. Such diverse carriers may be blended in a dosage form to achieve a desired performance. In addition, the dosage form release profile may be effected by a polymeric matrix composition, a coated matrix composition, a multi-particulate composition, a coated multi-particulate composition, an ion-exchange resin-based composition, an osmosis-based composition, or a biodegradable polymeric composition.

While manufacture of implementations of particular implementations of ecdysterone compounds have been described in particular sequences of steps and/or in particular forms, it will be understood that such manufacture is not limited to the specific order of steps or forms as disclosed. Any steps or sequences of steps of manufacture of particular implementations of ecdysterone compounds in any form are given as examples of possible steps or sequences of steps or potential forms and not as limitations, since many possible manufacturing processes and sequences of steps may be used to manufacture particular implementations of ecdysterone compounds in a wide variety of forms.

Use

The various particular implementations of ecdysterone compounds disclosed herein are particularly useful in increasing the bioavailability of ecdysterone, increasing the half life of ecdysterone, and increasing the distribution of ecdysterone to skeletal muscle tissue. The foregoing benefits exist with respect to both ecdysterone and other ecdysteroids disclosed herein, as well as with respect to both single-administration ecdysterone and in conjunction with other known ecdysterone compositions. By way of non-limiting example, in some particular implementations, a human dosage of an ecdysterone compound may equal about 1 mg of ecdysterone compound for kilogram of subject body weight. Notwithstanding, considering the enhanced characteristics of various ecdysterone esters (relating at least to enhanced bioavailability, half life and distribution), as compared to single-administration ecdysterones, the dosage for ecdysterone esters may be less than for single-administration ecdysterone. By way of non-limiting example, a minimum effective dose of an ecdysterone ester may be as little as 0.1 mg/kilogram of body weight in the case of ecdysterone deaconate. In addition, a minimum effective dose of an ecdysterone ester may be as little as 0.3 mg/kilo of body weight in the case of ecdysterone isobutyrate. Also, a minimum effective dose of an ecdysterone ester may be as little as 0.5 mg/kilo of body weight in the case of ecdysterone acetate. Since potential ecdysterone benefits may be dependent upon the size of the dose administered, and since many ecdysterone compounds may exhibit low relative toxicity, a user may have great flexibility in increasing a dose of an ecdysterone compound to achieve a desired level of anabolic activity.

Current ecdysterone administration protocols include intramuscular/intravenous injection (with the former being more beneficial for muscle growth), oral delivery, sublingual delivery (which may be comparatively less effective, both because of the low transportation capacity of the sublingual mucus, as well as the low lipophilicity of ecdysterone), along with various ointment/cream preparations for the healing of external wounds.

Specifically, the applicants have discovered that the effectiveness of oral administration of ecdysteroids in humans may be increased by one or more of: increasing the bioavailability of ecdysterone; increasing the half life of ecdysterone; and/or increasing the distribution of ecdysterone to skeletal muscle tissue. Notwithstanding the foregoing, particular implementations of ecdysterone compounds are not limited to uses relating to increasing the bioavailability of ecdysterone, increasing the half life of ecdysterone, and/or increasing the distribution of ecdysterone to skeletal muscle tissue, and the like. Rather, any description relating to the foregoing is for the exemplary purposes of this disclosure. It will be understood that particular implementations of ecdysterone compounds may encompass a wide variety of uses and are not necessarily limited in their uses.

For example, possible further uses of particular implementations of ecdysterone compounds may include: increasing body protein synthesis; amelioration of psychological depression; enhancement of immune system; stimulation of carbohydrate metabolism; reduction of cholesterol levels; enhancement of liver function; restoration of urea balance; amelioration of renal dysfunction; reduction of DNA damage; enhancement of wound healing; cardiovascular system health; increasing antibiotic and antiviral activity; increasing antioxidant and anti-aging activity; resistance of arrhythmia; increasing personal energy; and/or enhancing male sexual potency.

With respect to the administration of conventional ecdysterone preparations, the limited bioavailability of ecdysterone, the limited half-life of ecdysterone, and/or the limited distribution of ecdysterone to skeletal muscle tissue has been observed in many patients. Such limitations of ecdysterone, whether in a single-administration form or in a known ecdysterone composition, are unfortunate at least because the effectiveness of ecdysterone (which might otherwise manifest physiological effects upon its administration) may well be limited by such low bioavailability, short half life (as compared to the particular implementations of ecdysterone compounds described herein), and low distribution to skeletal muscle tissue.

Accordingly, Applicants have discovered that the particular implementations of ecdysterone compounds disclosed and made possible by the disclosures herein, when administered, provides enhanced bioavailability of ecdysterone, increased half life of ecdysterone, and enhanced distribution of ecdysterone to skeletal muscle tissue.

What is claimed is:

1. A method for increasing in a human one of: bioavailability of ecdysterone; half-life of ecdysterone; and distribution to skeletal muscle tissue of ecdysterone, the method comprising administering an effective amount of a physiologically active ester of ecdysterone to the human.

2. The method of claim 1, wherein administering an effective amount of a physiologically active ester of ecdysterone to the human comprises administering ecdysterone decanoate in a range from about 0.1 milligram per kilogram of body weight to about 1.0 milligram per kilogram of body weight.

3. The method of claim 1, wherein administering an effective amount of a physiologically active ester of ecdysterone to the human comprises administering ecdysterone decanoate in a range from about 1.0 milligram per kilogram of body weight to about 10.0 milligrams per kilogram of body weight.

4. The method of claim 2, wherein administering an effective amount of a physiologically active ester of ecdysterone to the human comprises administering via injection an effective amount of ecdysterone decanoate.

5. The method of claim 2, wherein administering an effective amount of a physiologically active ester of ecdysterone to the human comprises administering orally an effective amount of ecdysterone decanoate.

6. The method of claim 1, wherein administering an effective amount of a physiologically active ester of ecdysterone to the human comprises administering ecdysterone isobutyrate in a range from about 0.1 milligram per kilogram of body weight to about 1.0 milligram per kilogram of body weight.

7. The method of claim 1, wherein administering a pharmaceutically effective amount of a physiologically active ester of ecdysterone to the human comprises administering ecdysterone isobutyrate in a range from about 1.0 milligram per kilogram of body weight to about 10.0 milligrams per kilogram of body weight.

8. The method of claim 6, wherein administering an effective amount of a physiologically active ester of ecdysterone to the human comprises administering via injection an effective amount of ecdysterone isobutyrate.

9. The method of claim 6, wherein administering an effective amount of a physiologically active ester of ecdysterone to the human comprises administering orally an effective amount of ecdysterone isobutyrate.

10. The method of claim 1, wherein administering an effective amount of a physiologically active ester of ecdysterone to the human comprises administering one of ecdysterone decanoate and ecdysterone isobutyrate from about 0.1 milligram per kilogram of body weight to about 10.0 milligrams per kilogram of body weight.

\* \* \* \* \*